US005263495A

United States Patent [19]

Butterfield

[11] Patent Number: 5,263,495

[45] Date of Patent: Nov. 23, 1993

[54] MOVING HARNESS AND METHOD OF USE

[76] Inventor: Ida M. Butterfield, 1026 Buchanan, Yuba City, Calif. 95991

[21] Appl. No.: 891,399

[22] Filed: May 29, 1992

[51] Int. Cl.[5] .......... A61G 15/00; A61F 5/37

[52] U.S. Cl. .......... 128/845; 128/875

[58] Field of Search .......... 128/872-876, 128/845; 5/81.1, 89.1; 294/140, 149, 150, 153, 156, 157; 119/96

[56] References Cited

U.S. PATENT DOCUMENTS 1,050,257 1/1913 Trigg .
1,310,958 7/1919 O'Connor .......... 128/875
1,711,864 5/1929 Whidden .
1,816,262 7/1931 Ritter .
2,062,586 12/1936 Lawrence .
2,102,281 12/1937 Pringle .
2,212,746 8/1940 Nunn .
2,480,314 8/1949 Benedict .......... 5/89.1
2,568,304 9/1951 Schoenbrun .
2,758,769 8/1956 Nunn et al. .
2,812,123 11/1957 Girton .
2,848,993 8/1958 Terrell .......... 128/875
2,900,976 8/1959 Kilmer .
2,956,641 11/1960 Rall .
3,046,982 7/1962 Davis .......... 128/875
3,458,878 8/1969 Combs .
3,563,208 2/1971 Nero .......... 119/96
3,669,107 6/1972 Posey .
3,829,914 8/1974 Treat .......... 5/81.1
3,884,225 5/1975 Witter .
3,889,668 6/1975 Ochs et al. .
4,273,215 6/1981 Leggett .
4,308,629 1/1982 Freemon .
4,396,013 8/1983 Hasslinger .
4,569,095 2/1986 Holling .
4,641,642 2/1987 Williams, Jr. .
4,655,207 4/1987 Ellis .
4,666,017 5/1987 Zimmerman .
4,667,624 5/1987 Smith .
4,675,925 6/1987 Littleton .
4,744,115 5/1988 Marchione .......... 5/81.1
4,759,311 7/1988 Boyle .
4,782,539 11/1988 Elliott .......... 5/89.1
4,788,941 12/1988 Villeneuve .......... 128/876
4,793,008 12/1988 Johansson .
4,872,226 10/1989 Lonardo .......... 5/81.1
5,014,374 5/1991 Williams .......... 128/876

*Primary Examiner*—Michael A. Brown
*Attorney, Agent, or Firm*—James M. Ritchey

[57] ABSTRACT

A device employed by a user for moving or guiding the position of a human wearer comprises first and second body belts with each terminating in first and second end regions. Associated with each body belt is a reversible coupling means, wherein when mated by the coupling means, the first and second first body belt end regions of each body belt form an adjustably sized and reversibly linked structure about the wearer. A central strap is attached to both the first and the second body belts, thereby producing a spacing segment along the central strap between the first and the second body belts. The central strap terminates in first and second end domains, wherein the central strap first end domain includes a variably sized first handle and the central strap second end domain includes a second handle.

11 Claims, 4 Drawing Sheets

MOVING HARNESS AND METHOD OF USE

FIELD OF THE INVENTION

This invention relates to a device for moving a person fitted with the subject harness. More specifically, the subject device comprises a graspable shoulder strap and side handles coupled to an upper body surrounding belt which is linked to a graspable lower body strap and side handles coupled to a lower body surrounding belt. Several shifting motions are made easier for a user by fitting a wearer with the subject device, including: elevating a medical patient's upper body or torso off the surface of an underlying support; dragging or lifting a wearer fitted with the subject harness by means of the associated handles and straps; rotating or rolling a wearer by means of the side handles; and similar actions.

DESCRIPTION OF THE BACKGROUND ART

Increasing interest is being focused on avoiding contact with body fluids having communicable agents such as the AIDS virus and the like. Individuals such as emergency paramedics, police, airline attendants, general medical personnel, and others engaged in handling and moving persons have, with increasing frequency, refused to touch individuals believed to have such communicable agents. Haphazard methods for moving individuals, such as placing a person on a blanket and having individuals lift or drag the blanket at the corners, have resulted in further endangerment to both the mover and movee.

Further, moving a person incapable of self movement or restricted to limited movement by reasons such as physical or mental disability, age, disease, injury, and the like has presented extreme difficulties for individuals with insufficient strength or leveraging ability. A common example is the necessity of inserting a chest board (an essentially rigid board that aids in insulating a patient from a supporting surface and provides a firm platform on which to perform CPR or similar procedures to the wearer or patient's exposed chest area) between a patient's back and an underlying supporting surface that required an unsuitable and often dangerous amount of critical time and effort. A medical staff member needed to grasp the wearer or patient and often struggle (especially if the patient was heavy and the staff member physically small) to lift the patient and then push the board into position. No suitable mechanical aids were available to assist the staff member in this difficult lifting and positioning process. Various harness devices exist for restraining or moving a person, but these prior art devices require ready access to the wearer's back region for fitting and usually demand the wearer's arms fit through small opening, neither of which are practical for a critically ill and possibly heavy wearer or patient.

U.S. Pat. No. 1,050,257 relates an elastic shoulder brace.

U.S. Pat. Nos. 1,310,958, 1,711,864, 1,816,262, 2,102,281, 2,212,746, 2,568,304, 2,758,769, 4,308,629, 4,666,017, 4,667,624, and 4,759,311 all disclose harnesses used with children for safety or restraining purposes.

U.S. Pat. Nos. 2,062,586, 4,655,207, and 3,669,107 present devices employed in restraining individuals.

U.S. Pat. Nos. 2,900,976, 3,458,878, 3,884,225, 3,889,668, 4,396,013, 4,569,095, 4,641,642, 4,675,925, and 4,793,008 all disclose medically related devices for moving, aiding, or securing patients.

U.S. Pat. Nos. 2,812,123, 2,956,541, and 4,273,215 describe and claim sports related harnesses.

U.S. Pat. No. 4,788,941 discloses a safety belt with multiple latches.

U.S. Ser. No. 07/821,476, by the subject inventor, comprises a method of moving the upper body of a patient for inserting a chest board before employing electric heart stimulation. The device utilizes a single chest belt having a shoulder strap and associated handle.

Copending patent application Ser. No. 07/874,115, by the subject inventor, discloses an upper body harness for moving an individual. The device comprises an upper body belt with side handles a and a shoulder strap with an associated handle.

SUMMARY OF THE INVENTION

An object of the present invention is to provide a device for quickly moving or rolling a patient or elevating a patient's upper body off the surface of an underlying support.

Another object of the present invention is to produce an inexpensive, compact, and optionally disposable device for assisting in moving a wearer into a shifted position by lifting, rotating, sliding, and the like.

An additional object of the present invention is to create a moving aid that permits one or more individuals to move a wearer of the subject harness.

Yet a further object of the subject harness is to provide a means for moving a patient, whereby contact with the person to be moved is minimized to prevent possible contamination by communicable agents and the like.

Yet another object of the present invention is to furnish a wearer or patient lifting device that may be fitted rapidly to a wearer or patient that is lying back down on a supporting surface without requiring access to the wearer or patient's back area.

Yet an additional object of the present invention is to provide a harness that includes color coded handles that emphasize the position to grasp for movement.

Yet still an another object of the present invention is to present a harness that is fitted to a person within a confined space, say an airplane seat, and then used to move that person to a more open area, say an airplane isle.

The subject invention, a harness, comprises a first body belt constructed from sturdy material terminating in first and second end regions and having a long axis extending between the first and the second end regions of the first body belt. Associated with the first body belt is a first coupling means for reversible mating, wherein when mated by the first coupling means, the first and second first body belt end regions form a reversibly linked structure about the wearer of adjustable perimeter size. Included is a second body belt constructed from sturdy material terminating in first and second end regions and a second coupling means for reversible mating, associated with the second body belt, wherein when mated by the second coupling means, the first and second second body belt end regions form a reversibly linked structure about the wearer of adjustable perimeter size. A central strap constructed from sturdy material and attached to both the first and the second body belts is provided, thereby producing a spacing segment along the central strap between the first and the second body belts. The central strap terminates in first and second end domains, wherein the central strap first end domain includes a first handle constructed from sturdy material and the central strap second end domain includes a second handle constructed from sturdy material. Third and fourth handles, constructed from sturdy material, are attached to the first body belt. Fifth and sixth handles, constructed from sturdy material, are attached to the second body belt. Also, means are associated with the central strap first handle for adjusting the first handle's size, whereby when the first handle is made longer the central strap spacing segment decreases in length and when the first handle is made shorter the central strap spacing segment increases in length.

Other objects, advantages, and novel features of the present invention will become apparent from the detailed description that follows, when considered in conjunction with the associated drawings.

DESCRIPTION OF THE PREFERRED EMBODIMENT

Figure 1:
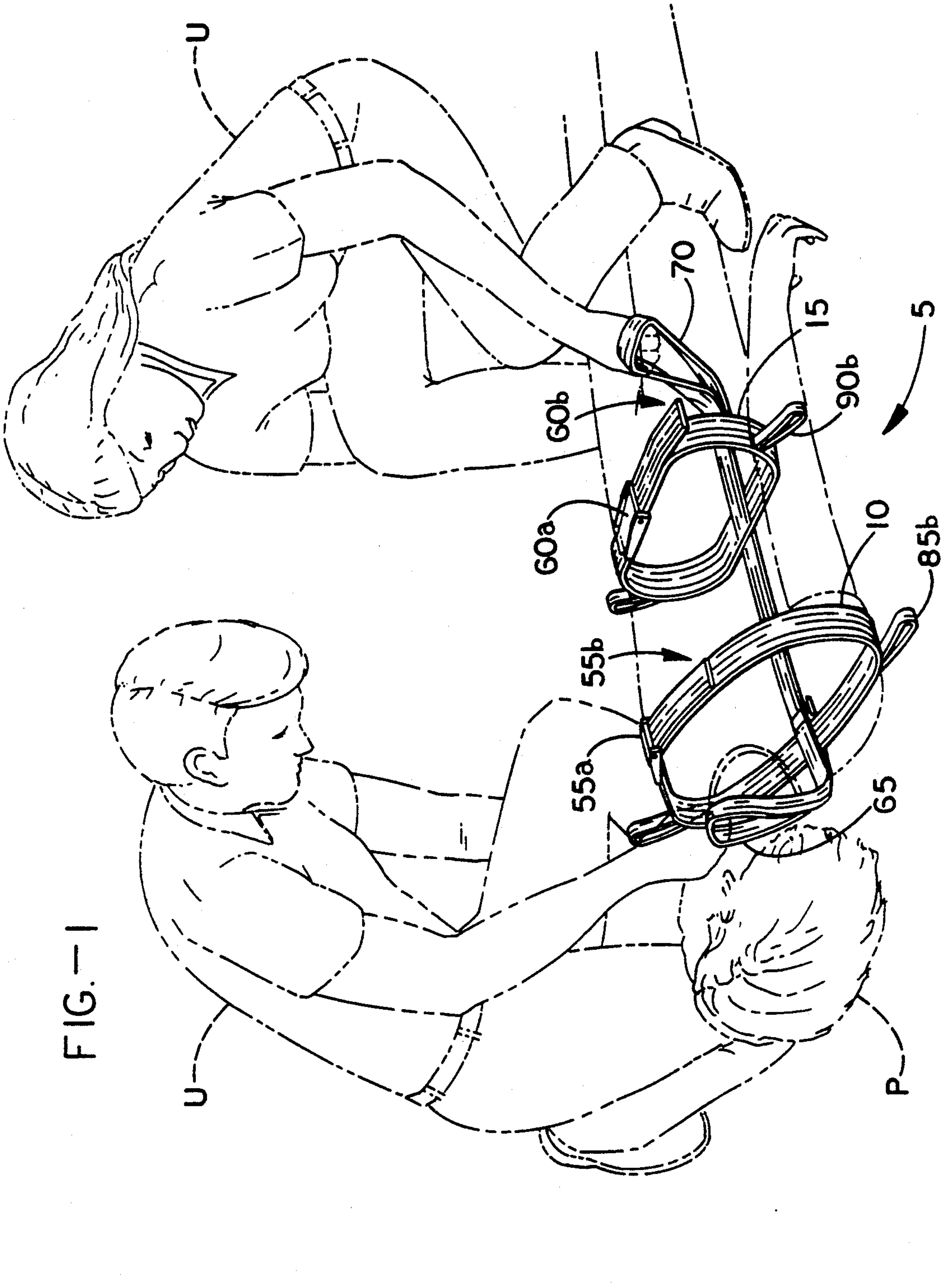
FIG. 1 is a perspective illustration of the subject device being fitted to a wearer.

Referring now to FIGS. 1–4 there is shown a preferred embodiment of a harness 5 of the subject invention. Three main components comprise the subject harness 5: a first body belt 10; a second body belt 15; and a central strap 20. The first body belt 10 terminates in first 25 and second 30 end regions and the second body belt terminates in first 35 and second 40 end regions. Likewise, the central strap 20 terminates in first 45 and second 50 end domains.

Each body belt 10 and 15 is a band-like strip, preferably of flattened and elongated rectangular proportions constructed from a sturdy material capable of withstanding the forces exerted by the heaviest wearer or patient. Suitable sturdy materials are woven or braided nylon or similar polymer, cloth, leather, or equivalent substances. The material should not have any appreciable stretch or be essentially non-elastic or non-resilient. Although each body belt 10 and 15 may be of any cross-sectional area, the flattened form is preferred. This flattened form permits a user to slip either or both body belts 10 and 15 easily under the body of a prone or reclining wearer or patient without the need of having free access to the wearer or patient's back area.

Figure 2:
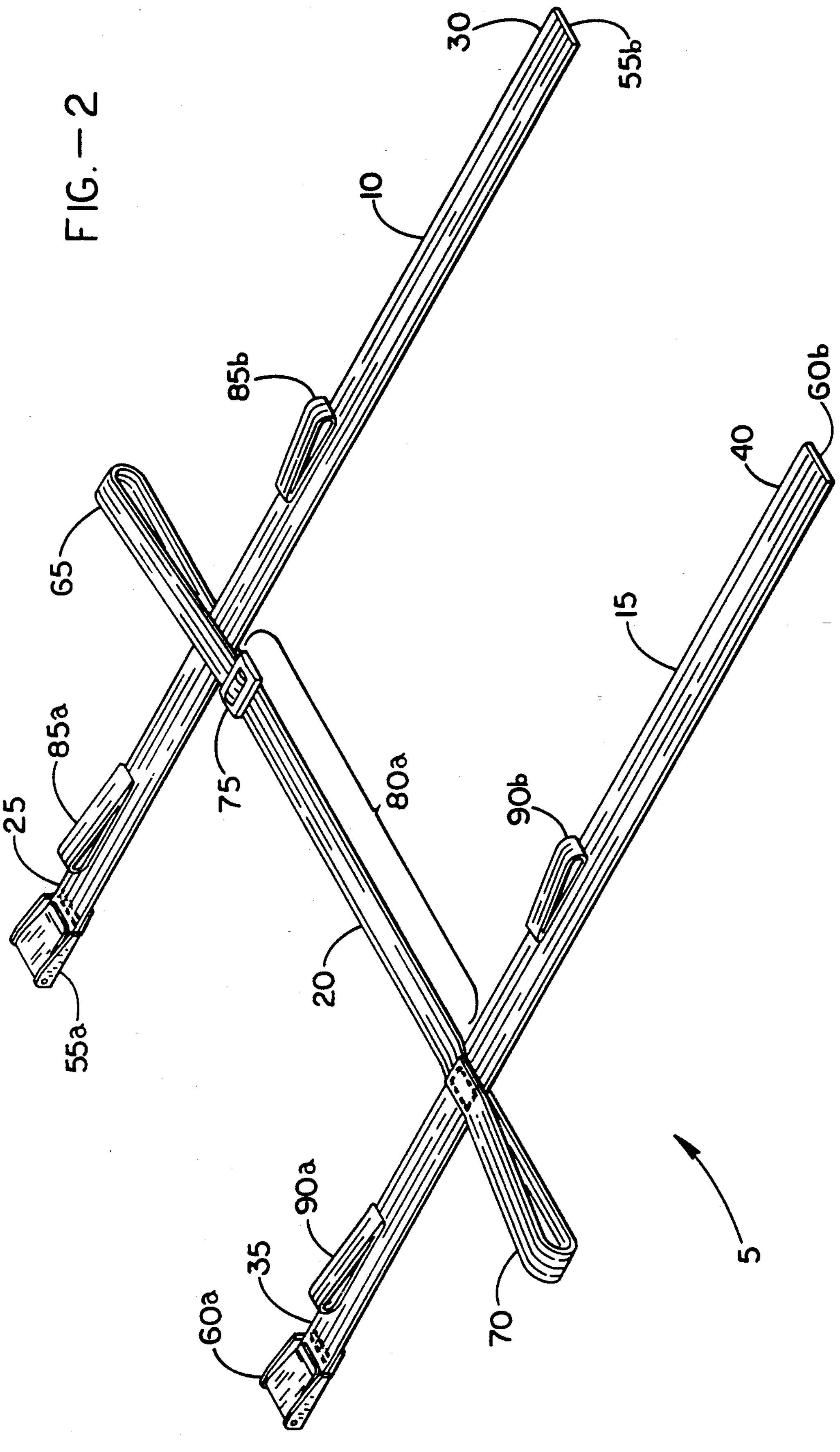
FIG. 2 is a perspective illustration of the outside of the subject harness device.
Figure 3:
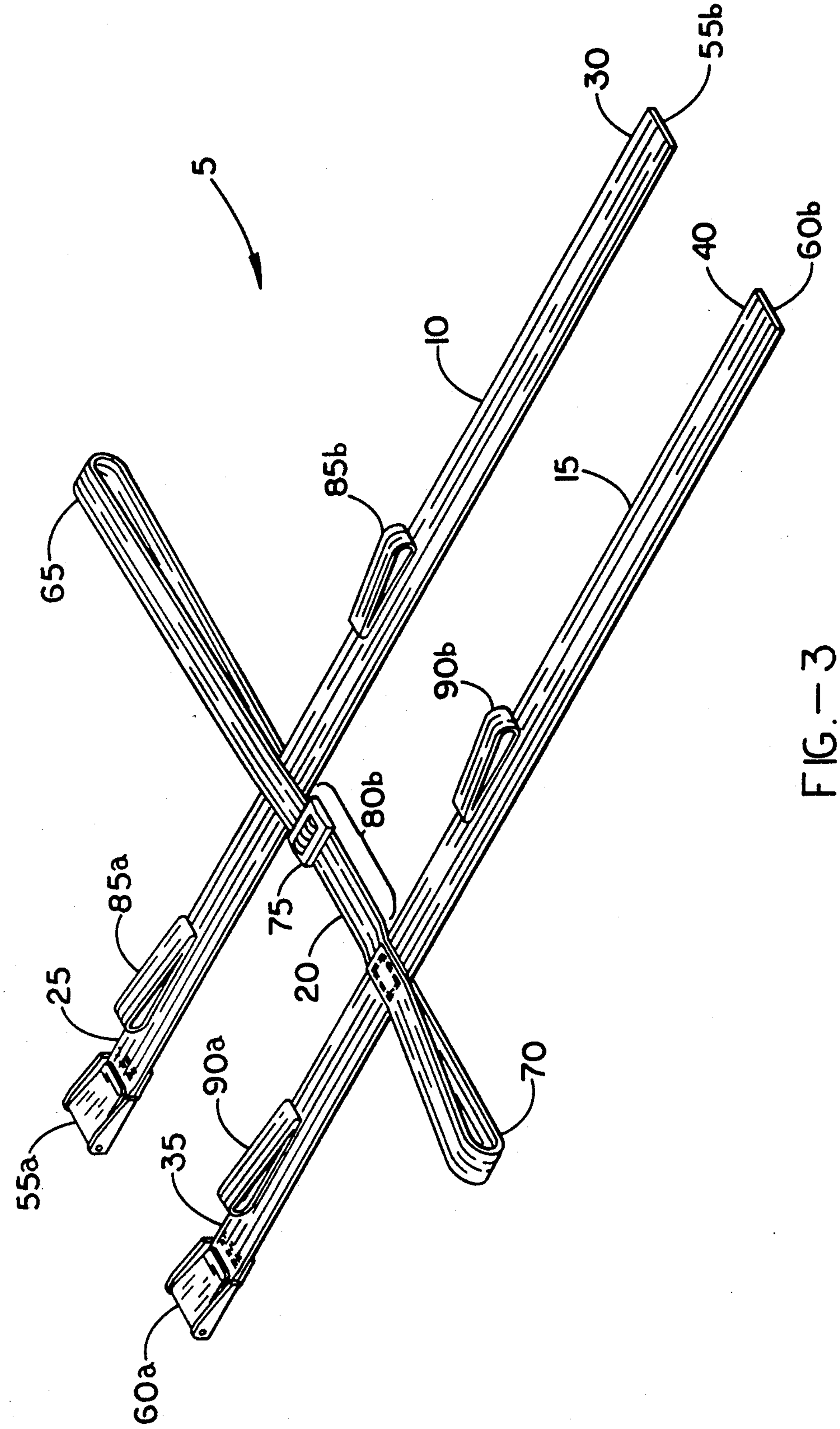
FIG. 3 is a perspective illustration of the inside of the subject harness with the shoulder strap in an elongated form.
Figure 4:
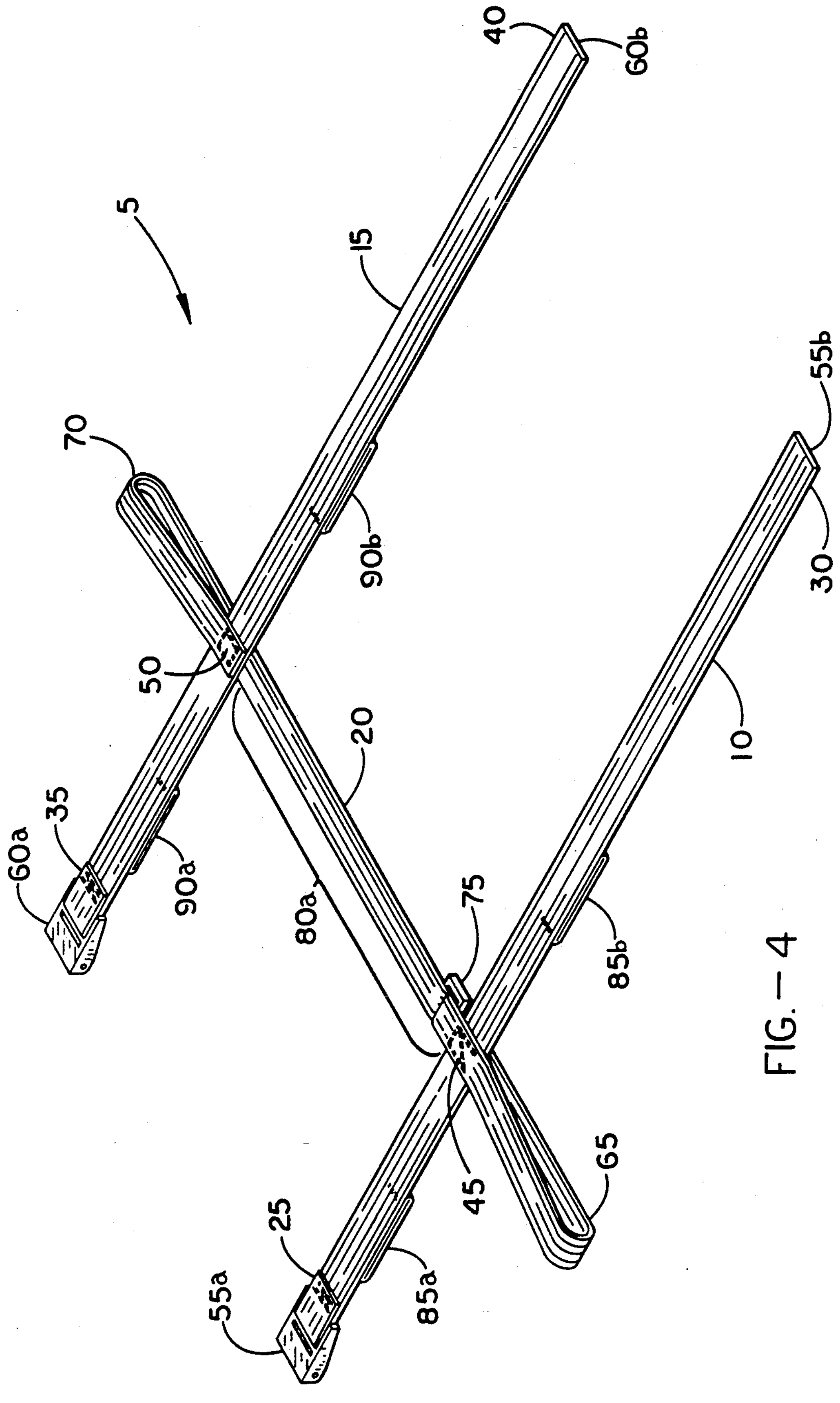
FIG. 4 is a perspective illustration of the inside of the subject harness with the shoulder strap in a shortened form.

For adjustably fastening and fitting each of the body belts 10 and 15 about the body of a person, a two half coupling means **55*a* and 55*b* is associated with the first body belt 10 and a two half coupling means 60*a* and 60*b* is associated with the second body belt 15 (see FIGS. 2–4). Specifically, coupling means half 55*a* is found in the first body belt first end domain 25, coupling means half 55*b* is found in the first body belt second end domain 30, coupling means half 60*a* is found in the second body belt first-end domain 35, and coupling means half 60*b* is found in second body belt second end domain 40**.

The coupling means (**55*a* with 55*b* and 60*a* with 60*b*) represent only one general type of coupling system and equivalent means are contemplated to be within the realm of this disclosure. As long as the coupling means provides a reversible mating link between the both of the two belt end domains, the coupling means is suitable. The coupling means serves to secure each belt 10 and 15 about a wearer or patient to form a reversibly linked structure (usually of approximately circular or oblong shape) of adjustable perimeter size. To facilitate a rapid fitting the coupling means is readily adjustable to fit the physical size of the wearer or patient. As shown in FIGS. 1–4, the coupling means (55*a* with 55*b* and 60*a* with 60*b*) comprises an unmodified first belt end 55*b* and 60*b* and a latch at the second belt end 55*a* and 60*a*. The first belt end region is inserted into the latch and the latch is clamped down by a leveraging action to engage and hold the belt closed. Another type of coupling system is a seat belt-like latch with mating male and female components, one associated with each belt end domain. The mating components of the coupling means are positioned, relative to each belt 10 and 15 and the wearer or patient, to mate on the easily accessible front or side areas of the wearer or patient. Further, in addition to the depicted coupling means 55*a* to 55*b* and 60*a* to 60*b*, other functionally equivalent coupling means may be employed, including a Velcro® mating pair, snaps, hooks and eyes, and like devices associated with the belt end domains. In particular, for a Velcro® mating pair having two members, each belt end domain 25 with 30 and 35 with 40 is attached to one of the mating members. The length of the Velcro® mating members is sufficient to allow the user to adjust each belt 10 and 15** to fit around the harnessed person.

The central strap 20 connects the two body belts 10 and 15. As seen in FIG. 4, the central strap first end domain 45 attaches to the first body belt 10 between the two first body belt end domains 25 and 30. Similarly, the central strap second end domain attaches to the second body belt 15 between the two second body belt end domains 35 and 40. Usually, each attachment is by sturdy stitching or equivalent means.

The central strap 20 then loops out from each end domain attachment 45 and 50 to generate a first handle 65 and a second handle 70. The first handle 65 is of variable size, as created by the included length adjustability means. Usually, the means for creating an adjustable length of the first handle is a buckle 75 secured to the first body belt 10 proximate the attachment point for the first end domain of the central strap 20. The central strap 20 fits through the buckle 75, thereby generating the looped first handle 65. The section of the central strap 20 located between the first 10 and second 15 body belts is a variable length spacing segment (see FIGS. 2 and 4 for an elongated spacing segment **80*a* and FIG. 3 for a shortened spacing segment 80*b*). Should a user desire to fit the subject device to a person's shoulder region and hip region, the spacing segment is elongated, thereby producing enough distance or length between the first 10 and second 15** body belts to span from the shoulders to hips.

Preferably, the second handle 70 is of a fixed size. The second handle 70 is produced by stitching (or an equivalent procedure) the central strap 20 once again to the second body belt 15. It should be noted that a variable length second handle, like the first handle 65, can be incorporated for the second handle, if the need should arise.

Although each handle 65 and 70 is depicted as a generalized loop, other variations are considered as within the scope of this disclosure.

Materials like those used to produce the belts 10 and 15 are appropriate for fabricating the central strap 20. Once again to attach the central strap 20 to the body belts 10 and 15 standard methods are employed such as stitching, riveting, gluing, heating, braiding, or equivalent procedures that are, preferably, permanent in nature (except for the central strap 20 adjustably sliding within the buckle 75 element).

Fabricated from the same sturdy, non-elastic materials as the central strap 20 and the body belts 10 and 15 are first body belt side handles 85*a* and 85*b* and second body belt side handles 90*a* and 90*b*. Although one side handle on each body belt is contemplated, preferably two side handles are securely attached to each body belt 10 and 15. One side handle 85*a* or 90*a* is attached to the body belt 10 or 15 between the central strap end domain 45 or 50 and the body belt first end domain 25 or 30. The other side handle 85*b* or 90*b* is attached to the body belt 10 or 15 between the central strap end domain 45 or 50 and the body belt second end domain 30 or 40. Each side handle 85*a*, 85*b*, 90*a*, and 90*b* is connected to the belt 10 or 15 by suitably strong means such as stitching, melting, riveting, or an equivalent method.

FIG. 1 illustrates the subject device 5 fitted to a person P that requires moving. Shown are two users U (often emergency paramedics, medical staff members, nursing home assistants, airline cabin personnel, firemen or firewomen, or similar individuals), one user U grasping the first handle 65 and the other user U grasping the second handle 70. Various fitting and grasping combination can be employed by the one or more users U employing the harness 5. Such fitting and grasping combinations include various lifting, turning, pulling, dragging, leveraging, and like forces exerted among the usually included six standard handles 65, 70, 85*a*, 85*b*, 90*a*, and 90*b*, lengthening and shortening the central strap 20, and employing one or both of the body belts 10 and 15. To fit the wearer with the harness 5 the belts 10 and 15 are forced beneath the person for fitting. It should be noted that in some cases only one of the belts 10 or 15 may be fastened around a person to be moved. If the person is lying down, each belt 10 and 15 is forced under the person's body at suitable body locations. Once the wearer has the belts 10 and 15 positioned under their back, the harness 5, specifically the belts 10 and 15, are fastened about the outer portion of the body to encircle the wearer. Each fastened belt 10 and 15 is adjusted by tightening or loosening the coupling means. After employing the harness 5 to move or guide a person, the harness 5 is removed.

Often in care homes for injured, elderly, disadvantaged, and like individuals a user of the subject harness 5 would fit the person with the harness 5 so as to use the harness 5 as a tool for guiding the individual from place to place. Also, the subject device 5 may be utilized as an assist in various physical therapy programs.

In emergency situations time is often a critical factor in a patient's survival. Any assistance in decreasing the time required to complete a critical medical procedure is highly important. To speed the use of the subject device color coding of important elements is included. Preferably, each handle 85*a*, 85*b*, 90*a*, and 90*b* is colored, usually red, to emphasize and indicate to the user exactly where to exert force. Further, usually, the central strap handles 65 and 70 are color coded to accentuate where force is to be exerted.

Due to the possible presence of various harmful contaminants, communicable diseases, and the like in medical settings, the subject device can be fabricated from materials suitable for disposal or sterilization.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. A harness employed by a user for shifting the position of a wearer, comprising:

a) a first body encircling belt constructed from sturdy material terminating in first and second end regions;

b) first coupling means for reversible mating associated with said first body belt, wherein when mated by said first coupling means, said first and second first body belt end regions form a reversibly linked structure around said wearer of adjustable perimeter size;

c) a second body encircling belt constructed from sturdy material terminating in first and second end regions;

d) second coupling means for reversible mating associated with said second body belt, wherein when mated by said second coupling means, said first and second body belt end regions form a reversibly linked structure around said wearer of adjustable perimeter size; and e) a central strap constructed from sturdy material and attached to both said first and said second body belts, thereby producing a spacing segment along said central strap between said first and said second body belts, wherein said central strap terminates in first and second end domains, wherein said central strap first end domain includes a first handle constructed from sturdy material and formed into a loop and said central strap second end domain includes a second handle constructed from sturdy material and formed into a loop.

2. A position shifting harness according to claim 1, further comprising at least one handle constructed from sturdy material attached to said first body belt.

3. A position shifting harness according to claim 2, wherein said first body belt handle is color coded to emphasize its location for rapid grasping by said user.

4. A position shifting harness according to claim 1, further comprising at least one handle constructed from sturdy material attached to said second body belt.

5. A position shifting harness according to claim 1, wherein said each said central strap handle is color coded to emphasize its location for rapid grasping by said user.

6. A position shifting harness according to claim 4, wherein said second body belt handle is color coded to emphasize its location for rapid grasping by said user.

7. A position shifting harness according to claim 1, wherein said central strap first handle includes means for adjusting both said first handle's size and said central strap spacing segment's length, whereby when said first handle is made longer said central strap spacing segment decreases in length and when said first handle is made shorter said central strap spacing segment increases in length.

8. A position shifting harness according to claim 7, wherein said central strap adjusting means comprises a buckle secured proximate said first body belt in which said buckle adjustably receives said central strap spacing segment.

9. A harness employed by a user for shifting the position of a wearer, comprising:

a) a first body encircling belt constructed from sturdy material terminating in first and second end regions;

b) first coupling means for reversible mating associated with said first body belt, wherein when mated by said first coupling means, said first and second first body belt end regions form a reversibly linked structure around said wearer of adjustable perimeter size;

c) a second body encircling belt constructed from sturdy material terminating in first and second end regions;

d) second coupling means for reversible mating associated with said second body belt, wherein when mated by said second coupling means, said first and second body belt end regions form a reversibly linked structure around said wearer of adjustable perimeter size;

e) a central strap constructed from sturdy material and attached to both said first and said second body belts, thereby producing a spacing segment along said central strap between said first and said second body belts, wherein said central strap terminates in first and second end domains, wherein said central strap first end domain includes a first handle constructed from sturdy material and said central strap second end domain includes a second handle constructed from sturdy material;

f) third and fourth handles constructed from sturdy material attached to said first body belt;

g) fifth and sixth handles constructed from sturdy material attached to said second body belt; and h) means associated with said central strap first handle for adjusting both said first handle's size and said central strap spacing segment's length, whereby when said first handle is made longer said central strap spacing segment decreases in length and when said first handle is made shorter said central strap spacing segment increases in length.

10. A position shifting harness according to claim 9, wherein said central strap adjusting means comprises a buckle secured proximate said first body belt in which said buckle adjustably receives said central strap spacing segment.

11. A position shifting harness according to claim 9, wherein said handles are color coded to emphasize their location for rapid grasping by said user.

* * * * *